United States Patent [19]

Imai

[11] 4,323,712

[45] Apr. 6, 1982

[54] ETHERIFICATION OF OLEFINIC HYDROCARBONS

[75] Inventor: Tamotsu Imai, Mt. Prospect, Ill.

[73] Assignee: UOP Inc., Des Plaines, Ill.

[21] Appl. No.: 189,449

[22] Filed: Sep. 22, 1980

[51] Int. Cl.³ ............................................. C07C 41/05
[52] U.S. Cl. ................................................... 568/697
[58] Field of Search ........................................ 568/697

[56] References Cited

U.S. PATENT DOCUMENTS

| | | | |
|---|---|---|---|
| 1,968,601 | 7/1934 | Edlund et al. ....................... | 568/697 |
| 2,720,547 | 10/1955 | Wolff et al. .......................... | 568/697 |
| 3,821,315 | 6/1974 | Massie et al. ....................... | 568/697 |
| 3,825,603 | 7/1974 | Massie ............................. | 568/697 X |
| 3,966,586 | 6/1976 | Owen et al. .................. | 568/697 UX |

OTHER PUBLICATIONS

Chem. Abs. Subject Index 1967–1971, vol. 66–75, (phthalocyaninetetrasulfonic acid).

*Primary Examiner*—Howard T. Mars
*Attorney, Agent, or Firm*—James R. Hoatson, Jr.; Raymond H. Nelson; William H. Page, II

[57] ABSTRACT

Olefinic hydrocarbons may be etherified by reaction with an alcohol in the presence of a phthalocyanine sulfonic acid catalyst at reaction conditions which will include a temperature in the range of from about 30° to about 200° C. and a pressure in the range of from about 1 to about 100 atmospheres. The phthalocyanine sulfonic acids which are employed in this process may, if so desired, contain a metal component such as cobalt, vanadium, tin, nickel, etc. and may also be composited on a solid support such as charcoal.

13 Claims, No Drawings

ETHERIFICATION OF OLEFINIC HYDROCARBONS

BACKGROUND OF THE INVENTION

Ethers, find a wide variety of uses in the chemical field. Of the ethers, diethyl ether is perhaps the most widely known and used. For example, this ether is used in the manufacture of smokeless powder, medicine, as an anesthetic, as a solvent for fats, oils resins, waxes, gums and alkaloids, in perfumery, in the manufacture of plastics, as an alcohol denaturant, as an extractant in various processes, etc. Other ethers such as methyl ethyl ether, and methyl propyl ether are used as solvents and, in addition, an ether such as methyl tert-butyl ether has become increasingly important due to the fact that this ether possesses excellent properties as an additive to gasoline whereby the octane number is increased by the presence of this compound.

It has now been discovered that ethers may be produced in an etherification reaction utilizing olefinic hydrocarbons and alcohols as reactants by effecting the reaction in the presence of certain catalytic compositions of metal of the type hereinafter set forth in greater detail.

DETAILED DESCRIPTION OF THE INVENTION

This invention relates to a process for the preparation of ethers. More specifically, the invention is concerned with a process for the etherification of olefinic hydrocarbons by reacting said hydrocarbons with an alcohol in the presence of certain catalytic compositions of metal.

It is therefore an object of this invention to provide a process for the etherification of olefinic hydrocarbons. A further object of this invention is to provide a process for the reaction of olefinic hydrocarbons with alcohols in the presence of a catalyst.

In one aspect, an embodiment of this invention resides in a process for the etherification of an olefinic hydrocarbon which comprises reacting a hydrocarbon with an alcohol in the presence of a catalyst comprising a phthalocyanine sulfonic acid at etherification conditions, and recovering the resultant ether.

A specific embodiment of this invention is found in a process for the etherification of an olefinic hydrocarbon which comprises reacting isobutylene with methanol in the presence of a catalyst comprising cobalt phthalocyanine tetrasulfonic acid at a temperature in the range of from about 30° C. to about 200° C. and a pressure in the range of from about 1 to about 100 atmospheres, and recovering the resultant methyl tert-butyl ether.

Other objects and embodiments will be found in the following further detailed description of the invention.

As hereinbefore set forth, the present invention is concerned with a process for the etherification of olefinic hydrocarbons. The reaction between an olefinic hydrocarbon and an alcohol in the presence of a catalyst comprising a phthalocyanine sulfonic acid is effected at etherification conditions. The etherification conditions which are employed in the present process will include elevated temperatures in the range of from about 30° to about 200° C. or more and pressures ranging from 1 atmosphere up to about 100 atmospheres. When employing normally gaseous olefins as one of the starting materials, the operating pressure will preferably comprise the autogenous pressure of the olefin. However, if pressures greater than the autogenous pressure are employed, the olefin will provide only a partial pressure, the remainder of the desired operating pressure being afforded by the introduction of a substantially inert gas such as nitrogen, helium, argon, etc. into the reaction chamber. Likewise, if the olefin which is to be etherified is normally liquid in nature and superatmospheric pressures are employed, the pressures will likewise be afforded by the use of the substantially inert gases hereinbefore set forth. The etherification reaction will be effected during a predetermined residence time which will be dependent upon the various operating parameters of temperature, pressure and reactants, said reaction time usually being in a range of from about 0.5 up to about 10 hours or more in duration.

Examples of olefinic hydrocarbons which are employed as one of the reactants in the process of this invention will include olefinic hydrocarbons containing from 2 up to about 10 carbon atoms or more, both straight-chain and branched-chain compounds being included. Some specific examples of these olefinic hydrocarbons will include ethylene, propylene, 1-butene, 2-butene, isobutylene, 1-pentene, 2-pentene, isopentene, 1-hexene, 2-hexene, 3-hexene, 2-methyl-1-pentene, 3-methyl-1-pentene, the isomeric heptenes, octenes, nonenes, decenes, etc.

The aforementioned olefinic hydrocarbons are etherified by reaction with an alcohol, and preferably an aliphatic alcohol which contains from 1 to about 10 carbon atoms in the chain. Some specific examples of the alcohols which may be used will include methanol, ethanol, n-propanol, isopropanol, n-butanol, t-butanol, n-pentanol, sec-pentanol, n-hexanol, sec-hexanol, as well as the isomeric heptanols, octanols, nonanols, decanols, etc.

The compositions of matter which are used to catalyze the etherification reaction of the present invention will comprise phthalocyanine sulfonic acids. The phthalocyanine sulfonic acids may, if so desired, contain a metallic component and, if so desired, may also be composited on a solid support. In the event that the catalyst is not composited on a solid support, it will be soluble in the alcohol which is employed as one of the reactants, and may therefore be used as a homogeneous catalyst. Alternatively, if the catalyst is supported on a solid material, it will be used as a heterogeneous catalyst and therefore may be used in a fixed bed, moving bed, or slurry-type operation. Specific examples of these catalysts will include non-metal phthalocyanine sulfonic acids such as phthalocyanine monosulfonic acid, phthalocyanine disulfonic acid, phthalocyanine tetrasulfonic acid, etc; metal phthalocyanine sulfonic acids such as cobalt phthalocyanine monosulfonic acid, cobalt phthalocyanine disulfonic acid, cobalt phthalocyanine tetrasulfonic acid, vanadium phthalocyanine monosulfonic acid, vanadium phthalocyanine disulfonic acid, vanadium phthalocyanine tetrasulfonic acid, the corresponding magnesium, titanium, hafnium, tantalum, molybdenum, manganese, iron, nickel, platinum, palladium, copper, silver, zinc and tin phthalocyanine sulfonic acids etc. As hereinbefore set forth, if so desired, the phthalocyanine sulfonic acids may be composited on a solid adsorbent support in the event that the catalyst is to be used as a heterogeneous catalyst. These supports include the various and well-known solid adsorbent materials which are generally used as catalyst supports and will include the various charcoals which are produced by the destructive distillation of wood, peat, lignite, nut shells, bones, and other carbonaceous matter and preferably such charcoals as have been heat treated or chemically treated or both, to form a highly porous particle structure of increased adsorbent capacity, and generally defined as activated charcoals. In addition, the adsorbent materials which may be employed as supports for the acids will also include the naturally occurring clays and silicates as, for example, diatomaceous earth, fuller's earth, kieselguhr, attapulgus clay, feldspar, montmorillonite, halloysite, kaolin, and the like, and also the naturally occurring or synthetically prepared refractory inorganic oxides such as alumina, silica, zirconia, thoria, boria, etc., or combinations thereof as, for example, silica-alumina, silica-zirconia, alumina-zirconia, etc. The aforementioned catalysts which are utilized in the present process may be prepared according to any method well-known in the art. It is to be understood that the aforementioned olefinic hydrocarbons, alcohols, and phthalocyanine sulfonic acids are only representative of the class of compounds which may be employed, and that the present invention is not necessarily limited thereto.

The process of the present invention may be effected in any suitable manner and may comprise either a batch or continuous type operation. For example, when a batch-type operation is employed, a quantity of the alcohol, along with the particular catalyst, whether homogeneous or heterogeneous in nature, is placed in an appropriate reaction vessel as, for example, an autoclave of the rotating, mixing or stirring type. In addition, if the olefinic hydrocarbon which is to undergo etherification is in liquid form, it is also placed in the autoclave. However, if the olefinic hydrocarbon is in gaseous form, the autoclave is sealed and the olefinic hydrocarbon is then charged thereto in gaseous form until the desired amount and operating pressure has been attained. Following the addition of all of the reactants and catalysts as well as any extraneous inert gas which may be required to attain the desired operating pressure which has been charged to the reactor, the reactor is then heated to the desired initial operating temperature. The reactor and contents thereof are then maintained at the desired operating conditions within the range herein set forth for the predetermined operating residence time. At the end of this time, heating is discontinued and, after the apparatus has returned to room temperature, any excess pressure which may be present is discharged and the autoclave is opened. The reaction mixture is recovered and, depending upon the type of catalyst employed, is subjected to conventional means of separation which may include such steps as decantation, filtration, washing, distillation, recrystallization, etc. whereby the desired ether is separated from any catalyst, unreacted starting materials, unwanted side products, etc. and recovered.

It is also contemplated within the scope of this invention that the etherification reaction be effected in a continuous manner of operation. When this type of operation is employed, the starting materials comprising the olefinic hydrocarbons and the alcohol are continuously charged to a reaction zone which is maintained at the proper operating conditions of temperature and pressure. In the event that a homogeneous catalyst is employed, the catalyst may also be continuously charged to the reaction zone dissolved in the alcohol which is employed as one of the starting materials. In the event that the catalyst is heterogeneous in nature, it may be positioned in the reactant as a fixed bed, while the reactants are passed over the catalyst bed in either an upward or downward flow. If a moving bed type of operation is employed, the catalyst bed is passed through the reaction zone either concurrently or countercurrently to the flow of the reactants, while if a slurry type of process is employed, the catalyst is carried into the reaction zone as a slurry in one or both of the reactants. After passage through the reaction zone for a predetermined period of time, the reactor effluent is continuously withdrawn from said reaction zone and passed to conventional means of separation and recovery, any non-reacted starting materials and catalysts which are separated from the desired reaction products comprising an ether being themselves recovered and recycled to the reaction zone to form a portion of the feed stock.

Examples of the ethers which may be prepared according to the process of this invention will include: methyl ethyl ether, methyl isopropyl ether, methyl isobutyl ether, methyl tert-butyl ether, methyl sec-pentyl ether, methyl sec-hexyl ether, methyl sec-heptyl ether; diethyl ether, ethyl propyl ether, ethyl isopropyl ether, ethyl isobutyl ether, ethyl tert-butyl ether, ethyl sec-pentyl ether, ethyl sec-hexyl ether, ethyl sec-heptyl ether; propyl isopropyl ether, propyl isobutyl ether, propyl tert-butyl ether, propyl sec-pentyl ether, propyl sec-hexyl ether, propyl sec-heptyl ether; butyl isobutyl ether, butyl tert-butyl ether, butyl sec-pentyl ether, butyl sec-hexyl ether, butyl sec-heptyl ether, etc. It is to be understood that the aforementioned ethers are only representative of the class of products which may be obtained from the etherification reaction of the invention and that said invention is not necessarily limited thereto.

The following examples are given for purposes of illustrating the process of the invention. However, it is to be understood that these examples are given merely for purposes of illustration and that the invention also is not necessarily limited thereto.

EXAMPLE 1

In this example, 1.80 grams of a catalyst comprising cobalt phthalocyanine tetrasulfonic acid which had been purified by recrystallization from hydrochloric acid was placed in a 300 cc rotating autoclave along with 30 grams of methanol. The autoclave was sealed and 53.6 grams of isobutene was charged thereto to afford a 1:1 molar ratio of olefin to alcohol. The autoclave was then heated to a temperature of 70° C. and maintained in a range of from 70° to 73° C. for a period of 4 hours. At the end of the 4 hour period, heating was discontinued and the autoclave was allowed to return to room temperature. The excess pressure which had been 24 atmospheres initially was discharged, the autoclave was opened and the reaction mixture was recovered. Analysis of the products by means of gas chromatography disclosed that there had been a 68% conversion of the isobutylene with a 100 mole percent selectivity to methyl tert-butyl ether.

The above experiment was repeated utilizing 1.8 grams of the catalyst, 30.0 grams of methanol, while 51.9 grams of isobutylene was charged to the reactor to afford an initial pressure at room temperature of 29 atmospheres. The autoclave was heated to a temperature of 100° C. and maintained thereat for a period of 4 hours. At the end of the 4 hour period, heating was discontinued, the autoclave was allowed to return to room temperature, and the excess pressure was discharged. After recovering the reaction mixture, it was subjected to gas chromatographic analysis which disclosed a 72% conversion of the isobutylene with a mole selectivity to methyl tert-butyl ether of 100%.

EXAMPLE 2

In a manner similar to that set forth in Example 1 above, a catalyst comprising cobalt phthalocyanine tetrasulfonic acid composited on charcoal may be used to effect the etherification of isobutylene by reacting equimolar amounts of ethanol and isobutylene at a temperature of about 100° C. for a period of 4 hours whereby ethyl tert-butyl ether may be formed.

EXAMPLE 3

In this example, equimolar amounts of methanol and propene may be reacted in the presence of vanadium phthalocyanine tetrasulfonic acid at a temperature of about 75° C. for a period of 4 hours in a rotating autoclave. At the end of the 4 hour period the reaction mixture may be recovered and the desired ether comprising methyl isopropyl ether may be recovered therefrom.

EXAMPLE 4

In this example, cobalt phthalocyanine monosulfonic acid may be used to catalyze the etherification of propylene with butenol at a temperature of about 100° C. and a pressure of about 30 atmospheres for a period of 4 hours whereby butyl isopropyl ether may be formed therefrom.

EXAMPLE 5

In a similar manner, utilizing a process hereinbefore set forth in the above examples, phthalocyanine tetrasulfonic acid may be used to catalyze the etherification of 1-pentene with ethanol in a rotating autoclave at a temperature of about 100° C. for a period of 4 hours whereby ethyl sec-pentyl ether may be formed and recovered.

I claim as my invention:

1. A process for the etherification of an olefinic hydrocarbon containing from 2 up to about 10 carbon atoms which comprises reacting said olefinic hydrocarbon with an aliphatic alcohol containing from 1 to about 10 carbon atoms in the presence of a catalyst consisting essentially of a metal phthalocyanine sulfonic acid, wherein said metal is selected from the group consisting essentially of cobalt, vanadium, magnesium, titanium, hafnium, tantalum, molybdenum, manganese, iron, nickel, platinum, palladium, copper, silver, zinc and tin at etherification conditions, and recovering the resultant ether.

2. The process as set forth in claim 1 in which said etherification conditions include a temperature in the range of from about 30° to about 200° C. and a pressure range from about 1 to about 100 atmospheres.

3. The process as set forth in claim 1 in which said metal phthalocyanine sulfonic acid is cobalt phthalocyanine disulfonic acid.

4. The process as set forth in claim 1 in which said metal phthalocyanine sulfonic acid is cobalt phthalocyanine monosulfonic acid.

5. The process as set forth in claim 1 in which said metal phthalocyanine sulfonic acid is cobalt phthalocyanine tetrasulfonic acid.

6. The process as set forth in claim 1 in which said metal phthalocyanine sulfonic acid is vanadium phthalocyanine tetrasulfonic acid.

7. The process as set forth in claim 1 in which said metal phthalocyanine sulfonic acid is composited on a solid support.

8. The process as set forth in claim 7 in which said catalyst is cobalt phthalocyanine tetrasulfonic acid composited on charcoal.

9. The process as set forth in claim 1 in which said olefinic hydrocarbon is isobutylene, said alcohol is methanol and said ether is methyl tert-butyl ether.

10. The process as set forth in claim 1 in which said olefinic hydrocarbon is isobutylene, said alcohol is ethanol and said ether is ethyl tert-butyl ether.

11. The process as set forth in claim 1 in which said olefinic hydrocarbon is propylene, said alcohol is methanol, and said ether is methyl isopropyl ether.

12. The process as set forth in claim 1 in which said olefinic hydrocarbon is propylene, said alcohol is butanol, and said ether is butyl isopropyl ether.

13. The process as set forth in claim 1 in which said olefinic hydrocarbon is 1-pentene, said alcohol is ethanol, and said ether is ethyl sec-pentyl ether.

* * * * *